United States Patent [19] [11] Patent Number: 4,747,824
Spinello [45] Date of Patent: May 31, 1988

[54] HYPODERMIC ANESTHETIC INJECTION METHOD

[76] Inventor: Ronald P. Spinello, 523 Post Ave., Westbury, N.Y. 11590

[21] Appl. No.: 868,745

[22] Filed: May 30, 1986

[51] Int. Cl.⁴ .............................................. A61M 31/00
[52] U.S. Cl. ...................................... 604/51; 604/207; 604/154; 433/89
[58] Field of Search ................. 604/51, 152, 154, 207, 604/228, 20; 433/84–85, 89–90, 119

[56] References Cited

U.S. PATENT DOCUMENTS

| | | | |
|---|---|---|---|
| 3,395,704 | 8/1967 | Frey et al. | 604/154 |
| 3,924,335 | 12/1975 | Balamuth et al. | 433/119 |
| 3,971,375 | 7/1976 | Hill | 604/207 |
| 4,141,359 | 2/1979 | Jacobsen et al. | 604/20 |
| 4,323,066 | 4/1982 | Bourdon | 604/228 |
| 4,597,754 | 7/1986 | Thill et al. | 604/51 |

Primary Examiner—C. Fred Rosenbaum
Assistant Examiner—Gene B. Kartchner
Attorney, Agent, or Firm—Hoffmann & Baron

[57] ABSTRACT

A method and apparatus for effecting painless hypodermic needle administration of liquid anesthetics particularly in dentistry in which the needle is carried on a light wand and the anesthetic is delivered to the needle by motive means independently of the operator's fingers during penetration of the needle, with both the rates of penetration and expression of liquid being controlled to achieve intermediate numbing followed by a high rate of liquid expression, if desired, to achieve full anesthesia of the site.

4 Claims, 3 Drawing Sheets

HYPODERMIC ANESTHETIC INJECTION METHOD

This invention relates to hypodermic anesthestic injection apparatus and methods, particularly as applied to dentistry.

BACKGROUND OF THE INVENTION

Almost 100 years ago the excruciating pain of dental extraction, drilling and reconstruction was eliminated by the invention of local anesthetics. Ever since, however, one smaller but often agonizing pain has remained; ironically, it is the pain of the hypodermic injection itself. All practical attempts to eliminate it have failed. While narrow gauge, sharp hypodermic needles can be inserted into the soft fleshy tissues of say an upper arm essentially without pain save possible psychological pain, the pain of a hollow needle inserted into the hard, relatively inelastic gum and mouth tissues to engage the bone which carries the nerves to the teeth, is more often than not real. It is also complex. Pain can be felt when the needle first punctures the firm tissue and thereafter as the needle tip cuts through the tissue. Pain can be felt if the needle scrapes the bone membrane and even greater pain can be felt if the injected liquid mass distends and tears the tissue, particularly the interior tissue, away from the bone in one of the most sensitive portions of the body, before absorption and numbing occur. And pain can be felt if either the dentist or the patient or both are not steady, causing traumatic lateral displacement of the embedded needle.

The present state of the art in hypodermic anesthetic injections, particularly dental injections, is at best a hit or miss art reflecting the skill and luck of the operator rather than being a scientifically repeatable procedure. The tools are clumsy and ill-suited to their task, making the administration of local anesthetics in dentistry one of the less pleasant procedures for both the dentist and the patient alike.

The present invention has for its object to eliminate pain in all phases of and for all types of hypodermic anesthetic injection including four in dentistry considered most difficult and painful: the palatal, the mandibular, the interligamentary, and the maxillary anterior.

Another object of the invention is to provide a factory-sterilized, assembled and sealed hypodermic syringe sub-assembly of needle, handle and anesthetic vial, fully charged with anesthetic to provide an unbroken chain of sterility from manufacture to patient.

Another object of the invention is to provide a universal hypodermic syringe which can be used for all known dental injection procedures, which is pleasant and easy to use and which affords the dentist extraordinarily acute tactile response characteristics essential to good dentistry.

Another object of the invention is to provide a local anesthetic injection apparatus and method which reduces the amount of anesthetic required to perform dental procedures.

BRIEF DESCRIPTION OF THE INVENTION

Nerves exit from the brain as large bundles or trunks. Much like a tree, the major nerves branch into smaller bundles. This branching continues until finally the nerves become individual fibers and spread in and around the cells of most all tissues in the body. On a microscopic level each nerve fiber is composed of cells aligned end on end and interconnected at each end by a synapse. When a stimulus is applied to a nerve ending, an electrical impulse or signal is transmitted from nerve cell to nerve cell and regenerated across each synapse, until it reaches the brain, where it is interpreted as pain, cold, hot, etc. When a local anesthetic solution is applied to a nerve, it blocks the signal transmission. The brain therefore receives no sensory information from the part affected by the anesthetic. At the cellular level this effect is immediate. It is believed that it occurs when the anesthetic comes in contact with a nerve part, rendering it instantly inoperative.

It is the object of dental injections to render the nerve bundles which supply the teeth and supporting structures free of pain sensation. These nerve bundles pass from the brain through the jaw bone to the teeth and gums. In instances in which the bone is spongy such as in the upper jaw (maxilla) the anesthetic can be placed at the outside bone surface adjacent to the tooth. The solution is absorbed by the porous bone and infiltrates to the tooth nerve. In other instances where the jaw bone is dense as it is in the lower jaw (mandible), the dentist must either block the nerve before it enters the jaw or he may attempt to force the anesthetic into the ligament space between the tooth root and the bone.

In all cases there is a delay before the anesthetic solution penetrates through the various tissues, and until it disables all of the fibers in the nerve bundle. During the injection procedure the needle point severs through tissues which contain live nerve endings causing pain, the injected anesthetic solution stretches these same tissues causing pain, and if the needle is moved laterally in these same tissues, it causes pain, all before the nerves in the main trunk are blocked.

The present invention provides a means whereby the nerves are disabled in the area of the injection and in the path of the needle before pain sensation is perceived. The needle is held in a stabilized trajectory and advanced slowly at a rate preferably, for example, not to exceed 6 mm/sec. through the tissues, and a flow of anesthetic solution is established concomitantly at a constant slow rate of 0.25 to 1.0 cc. per minute, surrounding the moving needle with a sheathing of anesthetic solution. Since nerve disability is instantaneous, needle penetration cannot be perceived as pain. When the needle reaches bone, if the constant and painless rate of flow of anesthetic is continued, tissue numbness occurs prior to tissue stretching. Once the surrounding tissues have been rendered numb, the rate of flow can be increased to expedite the procedure.

The instrument in accordance with one preferred embodiment of the invention, includes a low-inertia needle and elongated handle assembly either connected by a flexible conduit to an anesthetic vial, or itself containing an anesthetic vial, all of which can be pre-sterilized and disposable; stabilizing means for referencing needle movement and position to the site; and an activator or pump to expel extremely small volumes of anesthetic at a controlled rate, from the vial to the needle tip and, selectively, relatively larger volumes at high flow rates.

The needle assembly can comprise a narrow pencil-grip handle to allow the thumb and forefinger of the operator to implant the needle delicately to sense the essential proximity to bone while the other fingers stabilize the needle assembly against a fixed reference such as the teeth. In the case of the mandibular injection which is deep in the sides of the mouth at the ascending ramus of the lower jaw bone and which seeks a small window in the bone to the large bundle of interior nerves serving all lower teeth, the handle can be stabilized to the lower jaw, either by the fingers of the dentist or by a bite block, thus relieving the dentist of the fatigue attendant a large volume (about 2 cc.) injection over a period of up to one minute. The needle can be moved axially for a controllable distance and direction without the loss of sensitivity by the fingers holding the unit. If desired, a movable pressure pad and needle guiding and shielding tip can be used to pre-engage the injection site as the needle is moved through it into the tissue, or it can be manually moved to expose only as much of the needle as is required for the injection.

The expression of extremely small amounts of the liquid anesthetic from the needle tip is critical at the outset of the injections. It is difficult if not impossible to achieve consistently low flow rates using a conventional thumb-actuated syringe, particularly while the needle tip, invisible to the dentist, is cutting through the tissue. In accordance with the invention, an initial flow rate on the order of 0.25 to 1.0 cc. per minute or approximately 0.5 to 1.5 drops per second (from a 30 gauge needle) is generated beginning not later than the outset of the initial needle penetration. This can be best achieved by separating the liquid pumping function from the hand which performs the needle implant. A foot-controlled motor is one preferred embodiment in which the motor is of variable speed and in which the anesthetic pumping action is bi-directional to achieve the essential test to determine that the needle is not implanted in a vein or artery when the high injection rate begins. The pumping action can be arranged so that the pressure of the anesthetic is reduced below the patient's blood pressure for a controlled interval, briefly and automatically for one or more times during each injection and in any event at the instant before high volume pumping begins in a fixed spot. This allows visible blood to flow into a viewing capillary in the syringe in the event the tip is implanted by error in a vein or artery.

BRIEF DESCRIPTION OF THE PRIOR ART

The sources of pain in hypodermic injections have long been recognized. Dental schools for example, teach care and steadiness in implanting the needle at precise locations, the need to achieve reverse flow to prevent injection of anesthetic directly into a vein, and an undefined slow injection rate, at least at first until numbness is achieved. The classic syringe instrument for doing all of this, a direct derivation from the medical intramuscular, subcutaneous and intravenous syringes, puts a heavy essentially unachievable burden on the dentist if the procedure is to be painless. The instrument is too heavy and it is held incorrectly to reflect optimum tactile sensations between the needle and the fingers of the dentist. It is all but impossible to achieve the uniformly low flow rates called for by the present invention. U.S. Pat. No. 1,046,166 suggests separating the anesthetic pumping and needle implanting functions by using the foot to pump the liquid. It achieves pressures beyond those achievable by the thumb to force the liquid into the tooth dentin, but is not concerned with low inertia, low precision-controlled flow rates and the combination of needle insertion and preliminary expression of anesthetic. U.S. Pat. No. 3,496,937 recognizes the advantage of a pencil grip and of at least partially freeing the thumb from the axial-thrust pumping action but at the expense of increased size and weight, and it lacks any way of achieving back-flow to test for insertion of the needle into a vessel. Also, the stored energy in the resilient (or elastomeric) container is such that maximum pressure and flow occur at the outset and decrease with time, which is the opposite of that which is required in accordance with the present invention. U.S. Pat. No. 966,128 discloses a power syringe adapted to be connected by a flexible rotating shaft to a dental lathe so that the dentist is freed from delivering the pumping forces. It does not disclose the method or apparatus whereby low, precision-controlled flow rates are established concomitantly with needle penetration, nor are selective high and low expression rates suggested. Overall, the prior art does not teach the combination of structures or the method which renders hypodermic anesthetic procedures repeatably painless and efficient for all types of injections.

DESCRIPTION OF PREFERRED EMBODIMENTS

Figure 1A:
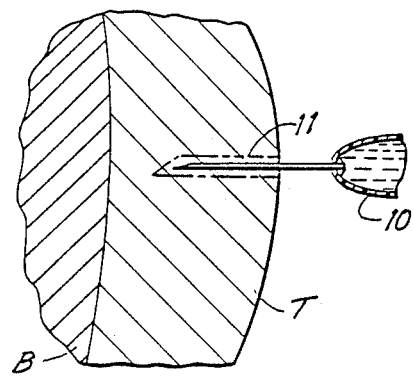
FIGS. 1A and 1B are diagrammatic representations in enlarged scale and in cross section illustrating the method of the invention as applied to one form of dental anesthesia.
Figure 1B:
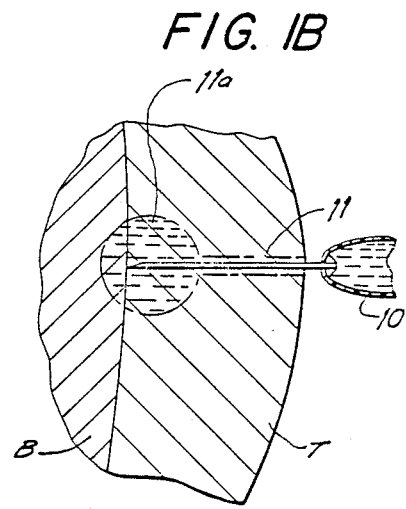
Figure 2A:
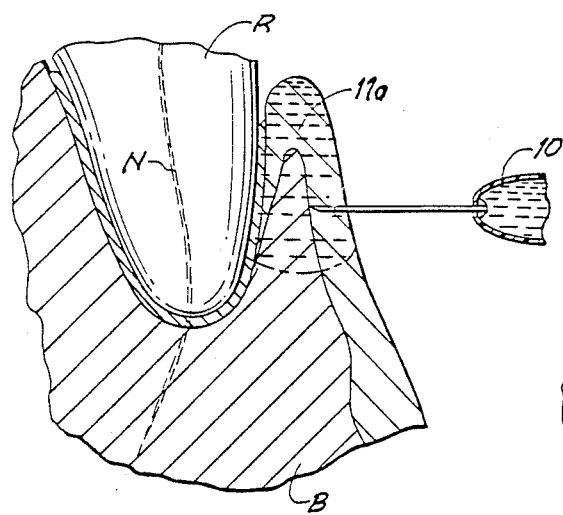
FIGS. 2A and 2B are diagrammatic representations in enlarged scale and in cross section illustrating the method of the invention as applied to an interligamentary dental anesthetic injection.
Figure 2B:
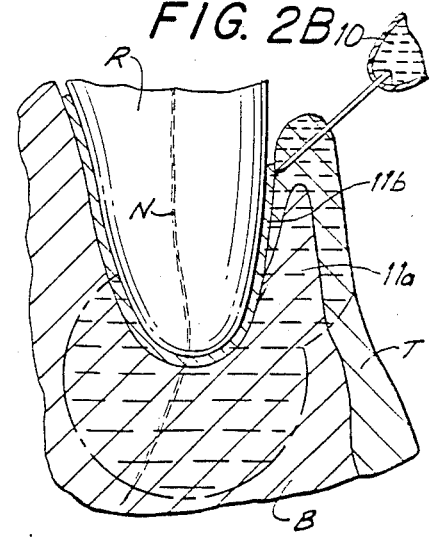
Figure 3:
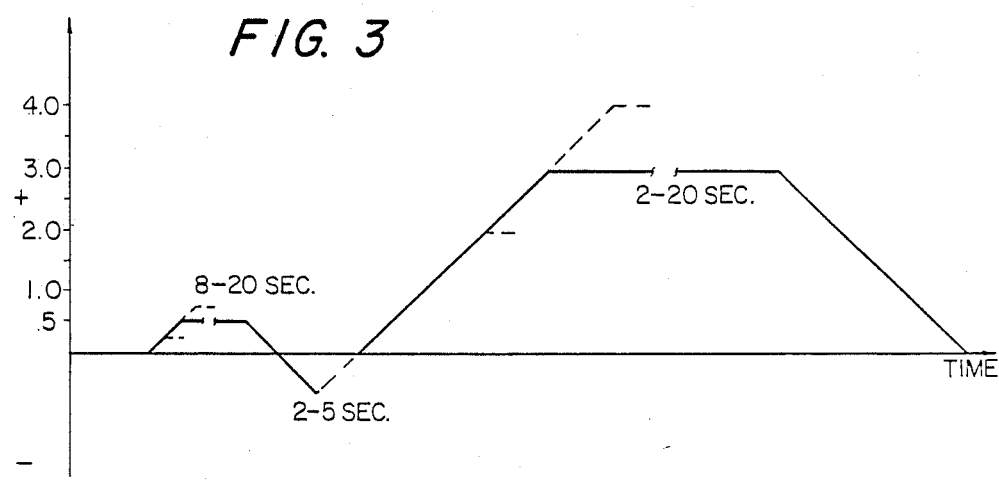
FIG. 3 is an anesthetic flow rate vs. time graph showing representative values for carrying out the invention.

The method of the present invention is described having reference to FIGS. 1 through 3. In FIGS. 1A and 1B the hollow pointed needle of a hypodermic syringe 10 is shown penetrating the soft gingival tissue T covering the bone B in which the root of a tooth (not shown) is imbedded. Prior to insertion of the needle into the tissue the syringe is filled with liquid anesthetic to the point at which a small drop appears at the opening in the tip of the needle. A flow rate for the anesthetic is then established through the needle in the range of 0.25 to 1.0 cc. per minute by means of apparatus described below. As the needle pierces the tissue preferably at a rate of penetration not exceeding 6 millimeters per second, anesthetic is expressed continuously and uniformly from the needle resulting in a sheath 11 of anesthetic from in front of the tip rearward which anesthetizes the path of travel of the needle rendering the insertion painless. When the needle reaches its desired position adjacent the bone, the relatively low continuous rate of anesthetic expression is continued creating a plume 11a constituting an expanded zone of tissue which is anesthetized due to infiltration of anesthetic into the soft tissue and the bone. This portion of the injection is termed "intermediate".

Referring to FIG. 3, this initial period of relatively low level anesthetic expression rate constituting the intermediate injection is shown on the time-rate graph as taking between 8 and 20 seconds, depending on the injection site and the particular requirements of the patient.

After the initial period of 8 to 20 seconds of low-rate injection of anesthetic the surrounding area becomes sufficiently anesthetized to enable the operator to increase the rate of flow to 2 to 4 cc. per minute until the desired degree of numbing is achieved. Such high rates of anesthetic expression normally cause pain due to stretching and tearing of the tissues, but having been pre-anesthetized no sensation is felt. Prior to beginning the high rate of injection a negative pressure relative to veinal blood pressure of the patient is established at the needle tip to reverse the fluid flow back into the syringe where it can be viewed by the operator for the presence of blood indicating a vein or artery has been entered which requires that the needle be repositioned. As shown in FIG. 3, the timing for the negative pressure phase can be on the order of 2 to 5 seconds. The actual reverse flow or aspiration of fluid represents the small total volume needed to fill the needle and viewing area beyond. The high speed expression of anesthetic, if needed, can be for a duration of 2 to 20 seconds depending on the nature of the injection. A mandibular injection at the ascending ramus of the lower jaw, for example, usually requires a full 2 cc. injection in a site deep within the lower jaw and takes the maximum time. The elapsed time of course varies with the rate of flow the upper limit of which is determined by the ability of the site to absorb the anesthetic liquid without creating such a large volume of unabsorbed liquid at the needle tip that tissue is torn from the bone.

Referring to FIGS. 2A and 2B, in which like parts are identified by like reference characters, there is illustrated an injection known as interligamentary, a normally difficult and painful injection in which anesthetic is forced under high pressure through the ligament space 11b between the bone and the roots of the tooth to the nerve N which enters the tooth at the root tip. The injection site is prepared by an intermediate injection using the low continuous flow rate of between 0.25 and 1 cc. per minute as the needle is inserted and thereafter against the bone for a total of 8 to 20 seconds (FIG. 2A) to achieve preliminary numbing. The needle is then placed as shown in FIG. 2B and a brief high speed injection rate of 2 to 4 cc. per minute is established to drive the anesthetic to the nerve N via the periodontal ligament space 11b. This enables the dentist to anesthetize an individual tooth for treatment with a minimum amount of anesthetic. The apparatus described below provides the flow rate and pressure necessary to achieve this injection method.

Figure 4:
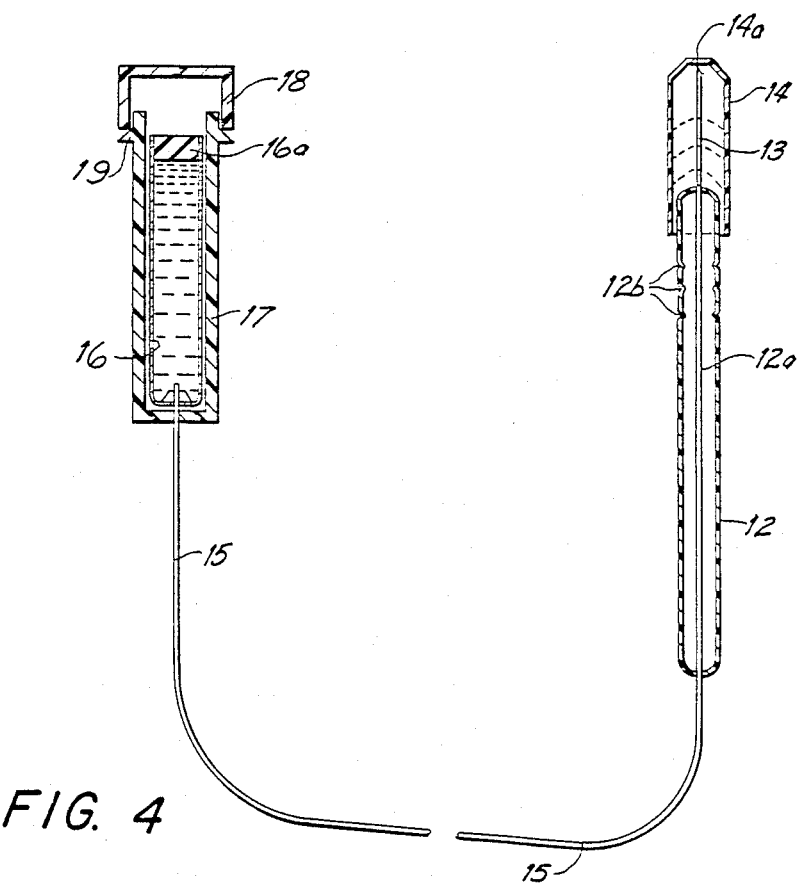
FIG. 4 is a drawing partly in cross section illustrating an expendable sterile pre-charged anesthetic and syringe kit in accordance with the invention.
Figure 5:
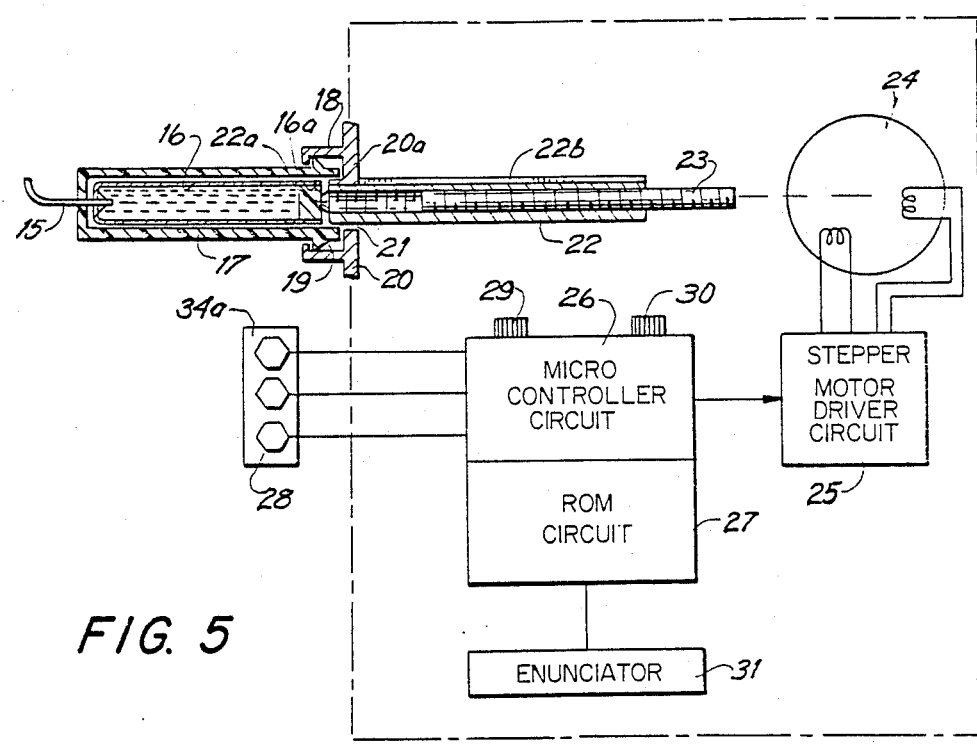
FIG. 5 is a schematic diagram partly in cross section illustrating one form of apparatus in accordance with the invention.
Figure 6:
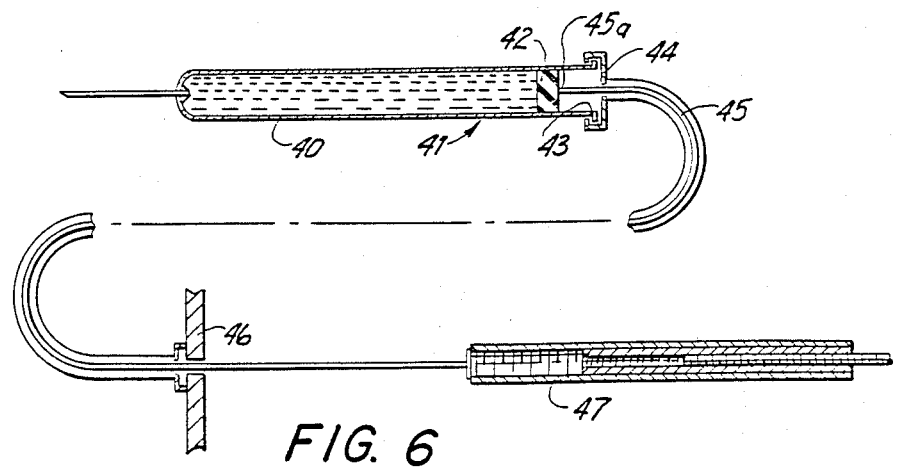
FIG. 6 is a schematic diagram illustrating another embodiment of the invention.

Referring to FIG. 4, there is illustrated an assembly of expendable parts comprising a sterile kit for one injection of anesthetic and used in conjunction with apparatus disclosed in FIGS. 5 and 6. The kit includes a handle or handpiece 12 carrying at one end a hollow hypodermic needle 13, preferably in range of 22 to 30 gauge, within a retractable transparent sheath 14 and connected at the other end to a length of flexible tubing 15. The handpiece 12 can be made of transparent plastic with a central bore 12a and is preferably in the range 8 to 18 centimeters in length and 20 to 50 millimeters in circumference.

The distal end of the tubing is connected to an anesthetic vial 16 which can be of conventional design formed of glass and containing a movable rubber piston 16a to seal in its 2 cc. anesthetic charge. The vial is housed in a transparent plastic container 17 sealed by a removable cap 18. The container includes a resilient rib 19 by means of which it can be mounted in the pumping apparatus of FIGS. 5 or 6 as described below.

The initial charge of anesthetic can if desired fill the tubing 15, the handpiece through-bore 12a and the hollow needle 14. With the sheath 14 and cap 18 in place the entire assembly can be factory-sterilized and sealed in a pouch for opening in the presence of the patient and discarded after one use. The sheath 14 includes a pierceable membrane 14a at its outer end so that it can be slid down the handpiece to expose three differing lengths of the needle in which position 1 constitutes an optimum length for an interligamentary injection, position 2 a maxillary injection and position 3 a mandibular injection. If desired indicia 12b can be formed on the handpiece 12 to indicate the three different positions in which the needle is stabilized to different degrees by the pierceable membrane.

Referring to FIG. 5 there is illustrated pumping apparatus for receiving the vial portion 16 of the assembly of FIG. 4 at a point remote from the patient but reachable by the flexible tubing 15. The plastic protective container 17 for the glass vial 16 is mounted in a yieldable coupling 18 so that the rib 19 secures the container and vial against axial movement with respect to a support 20. The support 20, which is part of a motor and motor controller housing (not shown), has an opening 21 through which passes a tubular piston rod 22, the outer end of which engages the rubber piston 16a in vial 16. A barbed tip 22a on the end of the piston enters the rubber piston to enable the piston to be withdrawn slightly when aspiration is called for. The piston rod is internally threaded to receive a drive screw 23 coupled to a reversible stepper motor 24. The piston rod 22 is axially slidably mounted in the support wall 20 and is constrained against rotation by a key 20a on the support and received in a slot or key-way 22b so that it is driven in and out upon activation of the stepper motor 24 to pump or aspirate depending upon the direction of rotation of the drive screw.

The stepper motor 24 is operated by a driver 25 controlled by a micro controller circuit 26 coupled to an ROM circuit 27 programmed to monitor the pulses to the stepper motor to establish limit stops for piston rod positions in and out. The circuit is also programmed to initiate an aspiration cycle, i.e., a small reverse motion for the piston 16a before every "fast" flow rate cycle. The fast, slow and reverse motions of the piston are controlled by the operator for slow, fast and reverse by means of switches 28 preferably foot-controlled or a combination of foot and manual control. The fast flow rate is geared to express liquid anesthetic from the needle tip at a rate of between 2 and 4 cc. per minute and the slow flow at 0.25 to 1.0 cc. per minute. The aspiration cycle is set to achieve in the form of reverse motion of the piston on the order of 1 to 2 mm. (or at least sufficient to draw back into the needle and the viewing portion of the handpiece viewable liquid drawn back from the tip of the needle to assure the operator that the needle has not been threaded into an artery or vein. This test must be done before the high rate of expression of anesthetic is commenced, whether it be immediately after the placement of needle in its final position or immediately before the high rate of expression is started. It must be gentle to avoid drawing the vein or artery wall against the opening in the needle.

The micro controller circuit includes manual push switches 29 and 30 for respectively, manually effecting rapid reverse of the piston rod for reloading and rapid forward for purging the system of air. An enunciator circuit for emitting a small audible tone upon the ejection of each, say, 0.5 cc. of anesthetic (measured by clocking the corresponding number of rotations of the shaft 23) provides a means of monitoring the injection without requiring the operator to look away from the site.

It will be understood that the apparatus of FIG. 5 is diagrammatic and can take various forms and arrangements. Reduction gearing can be provided between the motor 24 and shaft 23 if required to maintain constant discharge pressures which are particularly essential for the interligamentary injection requiring high pressure as well as a substantial flow rate to drive the anesthetic through the tooth ligament to the nerve at the root tip. Also, the threaded shaft 23 can be mounted to drive a threaded block follower carrying the piston rod in a laterally offset position relative to the threaded shaft and carried in its independent slide bearings.

In the arrangement of FIG. 6 the anesthetic vial and reservoir 40 is incorporated in the handpiece 41 together with a piston 42 and a coupling rib 43 adapted to be coupled to a drive rod head 44. A sheathed flexible drive rod 45 enters the head 44 and couples through a barbed tip 45a to the piston 42. The other end of the sheathed drive rod is connected to a motor housing 46, with the sheath being secured to the housing and the flexible push-pull drive rod being secured to a reciprocatable drive shaft 47 corresponding to the drive shaft 34 of FIG. 5. The switch controls and motor can also correspond to those of the system of FIG. 5.

While the invention has been described having reference to preferred embodiments it will be understood that it can take other forms and arrangements. For example, the controls for the motive means can take the form of low voltage electrical switches in the handpiece. In general, it is preferred that the handpiece be made light to afford the operator maximum tactile sensation for needle placement and to free the fingers for stabilization of the needle. Also, other means for driving the piston in the handpiece in the embodiment of FIG. 5 can be used such for example as a remote hydraulic pump connected by a hydraulic line to the back side of the piston. In such a system a double piston spaced by a spreader can be used to prevent leakage contamination. The invention should not therefore be regarded as limited except as defined in the following claims.

I claim:

1. A method for anesthetizing body tissue by means of local anesthetic using a hollow hypodermic needle, the steps of establishing a uniform flow of anesthetic at a flow rate less than 1.0 cc. per minute through the needle no later than the instant of entry into the tissue maintaining said uniform flow while moving the needle into the tissue, whereby said flow rate is sufficient to establish and maintain a sheath of liquid anesthetic around the forward portion of the moving needle thereby to anesthetize the path of travel of the needle.

2. The method of claim 1 including the steps of maintaining the flow rate beneath that which would displace and tear tissue and continuing the liquid discharge after the needle is fully implanted to form an anesthetic absorption plume around the needle tip to numb a localized space for further treatment.

3. The method of claim 2 including the step of thereafter increasing the rate of expression of liquid to drive the liquid to nerve sites within the localized numb area.

4. The method of claim 3 in which the increased flow rate is between 2 and 4 cc. per minute.

* * * * *